United States Patent [19]

Mesch et al.

[11] Patent Number: 5,037,474

[45] Date of Patent: Aug. 6, 1991

[54] BITUMEN ANTISTRIPPING AGENT

[75] Inventors: Keith A. Mesch; Larry M. Girdler, both of Cincinnati, Ohio

[73] Assignee: Morton International, Inc., Chicago, Ill.

[21] Appl. No.: 441,860

[22] Filed: Nov. 27, 1989

[51] Int. Cl.$^5$ .............................................. C08L 95/00
[52] U.S. Cl. ................................ 106/273.1; 106/284.1
[58] Field of Search ............... 106/284.1, 273.1, 281.1, 106/277, 278, 287.29; 252/174.16

[56] References Cited

U.S. PATENT DOCUMENTS

| | | | |
|---|---|---|---|
| 3,235,627 | 2/1966 | Mansfield et al. | 252/174.16 |
| 3,294,693 | 12/1966 | Dupre et al. | 252/174.16 |
| 3,869,412 | 3/1975 | Waag | 252/174.16 |
| 4,018,696 | 4/1977 | Hellsten et al. | 252/174.16 |

Primary Examiner—Theodore Morris
Assistant Examiner—Mary C. DiNunzio
Attorney, Agent, or Firm—Wayne E. Nacker; Gerald K. White

[57] ABSTRACT

A bitumen antistripping agent is prepared by reacting an epoxy compound with either phosphoric acid or a partial ester of phosphoric acid at a molar ratio of between 1:1 and 1:20.

18 Claims, No Drawings

BITUMEN ANTISTRIPPING AGENT

The present invention discloses bituminous compositions, such as those used in paving and roofing applications, comprised of a bitumen-containing material and the reaction product of an epoxy compound with phosphoric acid or a phosphoric acid partial ester. These compositions provide improved adhesion between aggregate materials and the bitumen-containing material.

BACKGROUND OF THE INVENTION

Bitumen may by generally described as a dark-brown to black cementitious material, solid or semi-solid in consistency, in which the primary constituents are a mixture of paraffinic and aromatic hydrocarbons and heterocyclic compounds containing sulfur, nitrogen and oxygen. As discussed in the *The Asphalt Handbook* (The Asphalt Institute Manual, Series No. 4, 1965 ed.), incorporated herein by reference, various grades of bitumen, including coal tar and asphalt, may be produced by selecting different processing conditions. In this regard, two basic types of solid asphalt, asphalt cement and air-blown asphalt, and two basic types of liquid asphalt, cutback asphalt and emulsified asphalt, are utilized commerically. Asphalt cement is defined as asphalt which has been refined to meet paving and industrial specifications; cutback asphalt is asphalt cement which has been liquified by blending with petroleum solvents, and asphalt emulsions are prepared such that the asphalt is emulsified in the inner phase (an oil-in-water type emulsion). The emulsion can also be of the water-in-oil type in which water constitutes the inner phase (see Hellsten et al., "Asphalt Compositions Having Improved Adhesion to Aggregate," U.S. Pat. No. 3,928,061).

The particle size of mineral aggregate used in an asphalt, compositions may vary over a wide range, such as from $2 \times 10^{-5}$ to $6 \times 10^{-2}$ meters in diameter; or the aggregate may be of a fairly uniform size. Mineral aggregates employed in asphalt compositions also range in character from hydrophilic to hydrophobic. It has long been known that mineral aggregates have a greater attraction from water than for oil or asphalt. In general, it can be said that siliceous and acidic minerals, such as sands and gravels, tend to be very hydrophilic, whereas calcareous and alkaline materials, such as limestone, tend to be slightly hydrophilic. It is difficult, therefore, to obtain and maintain a satisfactory asphalt coating on the mineral aggregate particles when water is present. One example of an asphalt composition is the combination of asphalt cement with a size-graded mineral aggregate. This combination is referred to as asphalt concrete and is used in road paving applications. A poor asphalt coating on the mineral aggreagate leads to breakup of the asphalt concrete and commonly results in potholes and flaking pavements.

One common method of pavement construction is to remove water from the aggregate by forced evaporation prior to coating with asphalt cement. In practice this requires a certain amount of aggregate drying time which consumes energy and may result in a lengthened construction period. If weather conditions are unfavorable, such as during periods of rainfall or high humidity, road construction may be severely hindered if not halted. Even if the water is removed and the asphalt successfully desposited onto the aggregate, the asphalt coating may ultimately be degraded by the action of groundwater or rainfall.

A successful method of increasing pavement life has been to add one or more antistripping additives to the asphalt composition. Such additives increase the hydrophobicity of the aggregate, thereby strengthening and preserving the asphalt-aggregate bond.

Recently, there have been some health-related concerns with volatiles resulting from the use in asphalt of some antistripping agents currently on the market. Less volatile and less odorous antistripping agents would be desirable.

SUMMARY OF THE INVENTION

It is discovered that the reaction product of phosphoric acid (or a phosphoric acid partial ester) with an epoxy compound is an effective antistripping agent for bitumen. The antistripping agent is used at a level of 0.05% to 5% relative to the weight of the bitumen.

DETAILED DESCRIPTION OF CERTAIN PREFERRED EMBODIMENTS

Herein, unless otherwise noted, all percentages are by weight and all percentages are expressed relative to weight of bitumen, exclusive of aggregate, solvent, other additives, etc. Bitument includes asphalt and coal tar. Of these, Generally asphalt is preferred.

In accordance with the invention, it is found that a reaction product of an epoxy compound with either phosphoric acid or a phosphoric acid partial ester is an effective antistripping agent for bitumen. Such antistripping agents minimize concerns of antistripping agent-derived volatiles from asphalt compositions.

The antistripping agent is described herein as the reaction product of (a) an epoxide compound or mixture of epoxide compounds each having the formula:

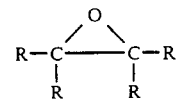

I.

wherein the R's are the same or different and are each selected from the group consisting —H, and $C_1$–$C_{20}$ alkyl, alkenyl, aryl, alkaryl and cycloalkyl; and a substance (b) selected from the group consisting of phosphoric acid, phosphoric acid partial acids and mixtures thereof, each having the general formula:

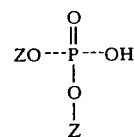

II.

wherein the Z's are the same or different and are each selected from the group consisting of —H, and $C_1$–$C_{20}$ alkyl, alkenyl, aryl, alkaryl, and cycloalkyl. Preferably in the expoxide compound of formula I, each of the R's is an alkyl or —H and most preferably each of the R's is —H. Preferably compounds of formula II are used in which each of the Z's is H or alkyl. The exact chemical structure of the reaction product is not determined; however, the compounds are believed to have the general formula:

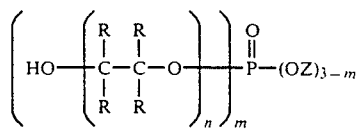

wherein m is from 1 to 3 and n is from 1 to 20.

The antistripping agents are produced by merely reacting the epoxy compound (a) with the phosphoric acid or with pre-formed phosphoric acid partial ester structures. This is typically accomplished by adding the epoxy compound to a solution of the phosphoric acid compound. The molar ratio of epoxy compound to phosphoric acid may vary from about 1:1 to about 20:1, a molar ratio in the range of from about 1:1 to about 5:1 being preferred. The molar ratio employed presumably determines the length of the polyglycol

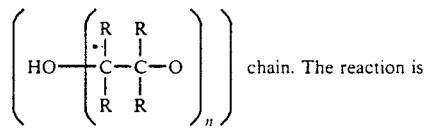

chain. The reaction is exothermic, and the reaction preferably is initially controlled, e.g., by rate of addition of the epoxy compound, to maintain a temperature in the range of 40° C. to about 90° C. Subsequent to complete addition of the epoxy compound, the temperature may be raised, e.g., to about 150° C. to 170 °C., to ensure that the reaction goes to completion and to help drive off water. A light vacuum may be employed at this stage to hasten the removal of water.

Water is initially present in association with the phosphoric acid or partial ester. When the reactant (b) is phosphoric acid, it is most practical to use the highly concentrated 85% solutions commerically available, as this minimizes the amount of water which must be driven off during and subsequent to the reaction. Likewise phosphoric acid partial esters are preferably used which have low volumes of water. Preferably, the antistripping additive finally contains less that about 4 wt. percent water.

To pre-form partial esters of phosphoric acid, phosphoric acid is esterified with an alcohol or alcohols. Useful alcohols are mono-hydroxyl alcohols having carbon chains, saturated, unsaturated, or aromatic, of between 1 and about 20 carbon atoms. The alcohol which is pre-esterified with the phosphoric is provided in a molar ration relative to the phosphoric acid of between about 1:1 and about 2:1. The product of the esterification is then reacted with epoxy compound as described above.

The antistripping agent is slightly water-soluble and slightly acidic in aqueous solution. This contrast with most common antistripping agents having amine, amide or amidoamine functionality, i.e., are alkaline.

The antistripping agents are added to bitumen, e.g., alphalt, at between about 0.05 wt. % to about 5 wt. % and preferably at levels of between about 0.2 wt. % and about 1.0 wt. %. It is felt that the antistripping agent is best utilized by adding it to hot liquid bitumen prior to mixing the bitumen with aggregates to prepare to common paving mixture. However, the antistripping agent may be used in bitumen as applied by other methods known in the art, e.g., as a solution in organic solvent or as a water-based latex emulsion.

The bitumen compositions in accordance with the present invention are admixed with conventional aggregates, such as crushed limestone, slag, crushed rock, sand, gravel, disintegrated granite, mineral filler, etc. Generally, bitumen, including additives, such as antistripping agents, is used at a level of between about 4 and about 6 wt. percent of a paving composition in which the balance is substantially all agregate.

The invention will now be described in greater detail by way of specific examples.

EXAMPLE 1

Additives were prepared by reacting ethylene oxide and phosphoric acid in various molar ratios. Ethylene oxide was bubbled through 85% phosphoric acid at a rate suitable to maintain a temperature range of 40° to 90° C. After the addition of all of the ethylene oxide, the temperature was raised to 160° C. and maintained thereat for 2–3 hours, during which heating period excess water was removed. The compounds were then added to asphalt at various levels.

The materials were then tested for performance by boiling water test method developed by the State of Georgia Department of Transporation to test ashpalt antistripping additives. The following table gives the results of these tests; a retained coating of 100% indicates no moisture damage.

| Additive Composition | Hrs. at 160° C. | Use Level | Percent Retained Coating |
| --- | --- | --- | --- |
| 1 None | — | — | 35 |
| 2 85% $H_3PO_4$ | — | .5 | 40 |
| 3 1M EO/1M $H_3PO_4$ | 0 | .5 | 60 |
| 4 1M EO/1M $H_3PO_4$ | 4 | .5 | 75 |
| 5 1.6M EO/1M $H_3PO_4$ | 0 | .5 | 80 |
| 6 1.6M EO/1M $H_3PO_4$ | 4 | .5 | 90 |
| 7 2.2M EO/1M $H_3PO_4$ | 0 | .5 | 60 |
| 8 2.2M EO/1M $H_3PO_4$ | 2 | .5 | 80 |
| 9 2.2M EO/1M $H_3PO_4$ | 2 | 1.0 | 97 |
| 10 PAVE BOND SPECIAL* | — | .5 | 90 |

*PAVE BOND SPECIAL is the registered trade name of a current high performance liquid antistripping additive for asphalt paving mixtures, sold by Morton International, Inc.

For these tests Granite Gniess Aggregate was coated with 7.0% A-C 30 asphalt containing the specified amount of additive.

EXAMPLE 2

The following table lists the results of some of the compositions of Examples 1 in the Indirect Tensile Splitting Test published by Robert P. Lottman in NCHRP Report 246, the state-of-the-art test method for determining moisture damage in paving mixtures. A tensile strength ratio of 1.00 indicates no moisture damage in this test:

| Additive Composition | Use Level | Tensile Strength Ratio Freeze-Thaw Cycles | |
| --- | --- | --- | --- |
| | | 1 | 3 |
| 1 None | | 0 | — |
| 4 1.6M EO/1M $H_3PO_4$ | 0.5 | 0.78 | 0.68 |
| 8 2.2M EO/1M $H_3PO_4$ | 0.5 | 0.98 | 0.86 |

-continued

| Additive Composition | Use Level | Tensile Strength Ratio Freeze-Thaw Cycles | |
|---|---|---|---|
| | | 1 | 3 |
| 10 PAVE BOND SPECIAL | 0.5 | 0.88 | 0.69 |

While the invention has been described in terms of certain preferred embodiments, modification obvious to one with ordinary skill in the art may be made without departing from the scope of the present invention.

Various features of the invention are met forth in the following claims:

What is claimed is:

1. A composition comprising (1) bitumen and based upon the weight of said bitumen, between about 0.05 and about 5.0 wt. percent of (2) the reaction product of (a) an epoxy compound or mixture of epoxide compounds wherein said epoxide compounds (a) have the formula:

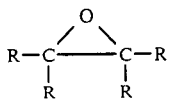

wherein the R's are the same or different are each selected from the group consisting —H, and $C_1$-$C_{20}$ alkyl, alkenyl, aryl, alkaryl and cycloalkyl, and a substance (b) selected from the group consisting of phosphoric acid, partial esters of phorphoric acid and mixtures thereof.

2. A composition according to claim 1 wherein the molar ratio of said epoxide compound (a) to said substance (b) is from about 1:1 to about 1:20.

3. A composition according to claim 1 wherein said R's are each alkyl or —H.

4. A composition according to claim 1 wherein said R's are each —H.

5. A composition according to claim 1 wherein said substance (b) has the formula:

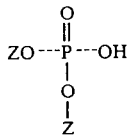

wherein the Z's are the same or different and are each selected from the group consisting of —H, and $C_1$-$C_{20}$ alkyl, alkenyl, aryl, alkaryl, and cycloalkyl.

6. A composition according to claim 5 wherein said Z's are each alkyl or —H.

7. A composition according to claim 5 wherein said Z's are each —H.

8. A composition according to claim 1 in which said reaction product (2) is the reaction product of phosphoric acid and ethylene oxide.

9. A composition according the claim 1 wherein the molar ratio of said epoxide compound (a) to said substance (b) is from about 1:1 to about 1:5.

10. A paving material comprising
(A) between about 4 and about 6 wt. percent of a composition comprising (1) bitumen, and, based upon the weight of said bitumen, between about 0.05 and about 5.0 wt. percent of (2) the reaction product of (a) an epoxy compound or mixture of epoxide compounds wherein said epoxide compounds(a) have the formula:

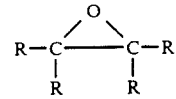

wherein the R's are the same or different and are each selected from the group consisting —H, and $C_1$-$C_{20}$ alkyl, alkenyl, aryl, alkaryl and cycloalkyl, and a substance (b) selected from the group consisting of phosphoric acid, partial esters of phorphoric acid and mixtures thereof; plus
(B) balance, substantially all aggregate.

11. A material according to claim 10 wherein the molar ratio of said epoxide compound (a) to said substance (b) is from about 1:1 to about 1:20.

12. A material according to claim 11 wherein said R's are each alkyl or —H.

13. A material according to claim 11 wherein said R's are each —H.

14. A material according to claim 10 wherein said substance (b) has the formula:

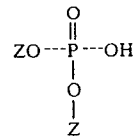

wherein the Z's are the same or different and are each selected from the group consisting of —H, and $C_1$-$C_{20}$ alkyl, alkenyl, aryl, alkaryl, and cycloalkyl.

15. A material according to claim 14 wherein said Z's are each alkyl or —H.

16. A material according to claim 14 wherein said Z's are each —H.

17. A material according to claim 10 in which said reaction product (2) is the reaction product of phosphoric acid and ethylene oxide.

18. A material according the claim 10 wherein the molar ratio of said epoxide compound (a) to said substance (b) is from about 1:1 to about 1:5.

* * * * *